(12) United States Patent
Kang et al.

(10) Patent No.: US 9,655,220 B2
(45) Date of Patent: *May 16, 2017

(54) CT DEVICES AND METHODS THEREOF

(71) Applicants: TSINGHUA UNIVERSITY, Beijing (CN); NUCTECH COMPANY LIMITED, Beijing (CN)

(72) Inventors: Kejun Kang, Beijing (CN); Chuanxiang Tang, Beijing (CN); Ziran Zhao, Beijing (CN); Zhe Zhang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/758,779

(22) PCT Filed: Oct. 31, 2013

(86) PCT No.: PCT/CN2013/086285
§ 371 (c)(1),
(2) Date: Jun. 30, 2015

(87) PCT Pub. No.: WO2014/101565
PCT Pub. Date: Jul. 3, 2014

(65) Prior Publication Data
US 2015/0342014 A1    Nov. 26, 2015

(30) Foreign Application Priority Data

Dec. 31, 2012  (CN) .......................... 2012 1 0592688
Jan. 28, 2013  (CN) .......................... 2013 1 0032983

(51) Int. Cl.
*A61B 6/00*    (2006.01)
*H05G 1/32*    (2006.01)
(Continued)

(52) U.S. Cl.
CPC ............... *H05G 1/32* (2013.01); *A61B 6/032* (2013.01); *A61B 6/4028* (2013.01);
(Continued)

(58) Field of Classification Search
USPC ....................................................... 378/4, 10
See application file for complete search history.

(56) References Cited

U.S. PATENT DOCUMENTS

| 2004/0108823 | A1 | 6/2004 | Amaldi et al. | |
| 2005/0111625 | A1 | 5/2005 | Lemaitre | |
| 2015/0342013 | A1* | 11/2015 | Kang | H01J 35/06 378/4 |

FOREIGN PATENT DOCUMENTS

| CN | 1736132 A | 2/2006 |
| CN | 101266217 A | 9/2008 |

(Continued)

*Primary Examiner* — Nicole Ippolito
*Assistant Examiner* — Hanway Chang
(74) *Attorney, Agent, or Firm* — Baker & Hostetler LLP

(57) ABSTRACT

CT devices and methods thereof are disclosed. The CT device comprises a circular electron gun array including a plurality of electron guns, each of the electron guns is configured to emit electron beams along the radial direction of the circular electron gun array in sequence according to a predetermine pulse sequence; an acceleration cavity disposed inside of a circle on which the circular electron gun array is positioned, including a plurality of nested concentric coaxial cavities that operate in π mode for accelerating electron beams emitted from the respective electron guns of the circular electron gun array; a circular transmission target disposed inside of a circle on which the acceleration cavity is positioned and being bombarded by the accelerated electron beams to generate X-rays; and a circular detector configured to receive the X-rays after they have passed through an object to be detected.

19 Claims, 2 Drawing Sheets

(51) Int. Cl.
*H05G 1/10* (2006.01)
*H05H 7/18* (2006.01)
*G01N 23/04* (2006.01)
*A61B 6/03* (2006.01)
*H01J 35/08* (2006.01)
*H05G 2/00* (2006.01)

(52) U.S. Cl.
CPC ......... *A61B 6/4275* (2013.01); *G01N 23/046* (2013.01); *H01J 35/08* (2013.01); *H05G 1/10* (2013.01); *H05H 7/18* (2013.01); *G01N 2223/419* (2013.01); *H01J 2235/087* (2013.01); *H05G 2/00* (2013.01)

(56) References Cited

FOREIGN PATENT DOCUMENTS

| | | |
|---|---|---|
| CN | 101352353 A | 1/2009 |
| CN | 101573157 A | 11/2009 |
| CN | 201418200 Y | 3/2010 |
| CN | 202305443 U | 7/2012 |
| CN | 203083953 U | 7/2013 |
| JP | 4517097 B2 | 8/2010 |
| WO | WO 2012/132156 A1 | 10/2012 |

\* cited by examiner

CT DEVICES AND METHODS THEREOF

CROSS-REFERENCE TO RELATED APPLICATIONS

This application is the National Stage of International Application No. PCT/CN2013/086285, filed on Oct. 31, 2013, entitled "CT DEVICE AND METHOD THEREOF," which claims priority to Chinese Patent Application No. 201310032983.2 filed on Jan. 28, 2013 and Chinese Application No. 201210592688.8 filed on Dec. 31, 2012, the disclosures of which are incorporated herein by reference in their entireties.

TECHNICAL FIELD

The present technique generally relate to the fields of medical imaging, industry detection and others. The technique may be directly applied to medial field that needs ultra-fast imaging, and also applied to industry field, such as non-destructive detection field.

BACKGROUND

CT, short for Computed Tomography, denotes a scanning technique to use a computer system to reconstruct a CT image of an object under detection, so as to obtain a three-dimension CT image. The scanning technique is to have rays of a single axial plane pass through the object under detection, collect transmitted rays by a computer system and reconstruct an image by a three-dimension reconstruction approach, where different parts of the object under detection have different absorptivities and transmissivities to the transmitted rays. The term "CT" used herein, if not specified otherwise, refers to an X-ray CT.

CT technique has five generations according to its development. The first four generations have a scanning part that can be implemented by a movable X-ray tube and a detector (mechanical scanning mode). The third generation and the fourth generation use a spiral scanning mode, and the scanning part used therein is comprised of a X-ray tube, a detector and a scanning stand on which the X-ray tube and the detector are mounted. In operation, the X-ray tube emits X-rays to an object to be scanned from periphery of the object by moving the scanning stand at a high speed, and a scanned CT image can be obtained after reception of the detector and processing of a computer system.

The spiral Multi-detector row CT (MDCT) that comes out in the recent years substantially belongs to the fourth generation CT, and has a scanning speed that is nearly the same as the spiral single-detector row CT. The rows of detectors, however, are increased, and thus multi-row data may be obtained by rotating the X-ray rube for one round. As for the well-developed MDCT of 64 rows, it needs 0.33 s to rotate for one round, and the temporal resolution is better than 50 ms (the temporal resolution mainly depends on the scanning period, and also on the scanning coverage and the reconstruction approach in the MDCT).

The foregoing fourth generation CT has an advantage of a high spatial resolution, but it also has a disadvantage of a low temporal resolution. The main factor that limits the temporal resolution is its scanning speed. As for the most advanced spiral MDCT, the maximal scanning speed is only 0.33 s/round, which depends on the mechanical strength limit of the scanning stand and the X-ray tube. When the CT rotates at a high speed, the line speed of the X-ray rube may be up to the first cosmic velocity. In order to ensure the stability of the structure, the rotation speed of the CT has a limit.

The fifth generation CT (UFCT) has a different scanning principle from the first four generations. An advanced electron beam technology is used to generate X-rays. The anode and cathode of the bulb tube are separate. Electron beams are emitted from the electron gun at the cathode, and are accelerated to form high-energy electron beams, which pass through a focusing and magnetic deflection coil, and project on the target surface of the anode which has a form of a 210° arc, and then X-ray beams are generated. Comparing with the conventional mechanical rotation, the scanning speed may be up to 50 ms/round.

In the medical imaging application, take the heart imaging as an example. If the mechanical scanning mode is used, one position will be scanned for 2 or 3 times within one second. If the electron beam scanning mode is used, one position will be scanned for 20 times within one second. In the industry detection application, the scanning time of performing CT on a large-scale object generally is several minutes.

In the existing CT imaging devices, there are three ways to increase the scanning speed: 1. Enhance hardware performance. For example, enhance the rotation speed of the mechanical structure, increase the number of ray sources, and others. 2. Perform equivalent scanning by means of the stability of the object to be detected. For example, the gating technique is used in the heart imaging. 3. Change the scanning mode to, for example, electron beam scanning (UFCT).

All the means may speed up the scanning speed to a certain extent, but cannot achieve ultra-fast scanning and CT imaging on an object that moves at a high speed.

SUMMARY

In view of the limit on the scanning speed (i.e., the temporal resolution) of the prior CT techniques, an object of the present technique is to provide a CT device of a high temporal resolution.

According to embodiments of the present technique, there is provided a CT device comprising a circular electron gun array including a plurality of electron guns, each of the electron guns is configured to emit electron beams along the radial direction of the circular electron gun array in sequence according to a predetermine pulse sequence; an acceleration cavity disposed inside of a circle on which the circular electron gun array is positioned, including a plurality of nested concentric coaxial cavities that operate in π mode for accelerating electron beams emitted from the respective electron guns of the circular electron gun array; a circular transmission target disposed inside of a circle on which the acceleration cavity is positioned and being bombarded by the accelerated electron beams to generate X-rays; and a circular detector configured to receive the X-rays after they have passed through an object to be detected.

According to embodiments of the present technique, the CT device may further comprise an electron gun control unit connected to the circular electron gun array and configured to generate the pulse sequence to control the circular electron gun array to generate electron beams that are emitted along the radial direction; a microwave power source connected to the acceleration cavity so that the electron beams are accelerated along the radial direction to have expected energy and bombard the circular transmission target to generate radial X-rays.

According to embodiments of the present technique, the electron gun control unit is controlled to change a trigger mode so as to change the scanning speed of the circular electron gun array.

According to embodiments of the present technique, the feed power of the microwave power source is adjusted to change the energy of the X-rays so as to generate X-ray beams of different energies.

According to embodiments of the present technique, the CT device may further comprise a control system coupled to the electron gun control unit and the microwave power source and configured to generate a control signal to control the electron guns in the circular electron gun array to start in sequence, and to control the microwave power source to generate microwave power for accelerating electron beams generated by the respective electron gun in sequence.

According to embodiments of the present technique, the CT device may further comprise a control system connected to the electron gun control unit and the microwave power source and configured to generate the control signal to control a first group of electron guns that are equally spaced in the circular electron gun array to start at a first timing simultaneously, to control a second group of electron guns that are equally spaced in the circular electron gun array to start at a second timing simultaneously, and to control the microwave power source to generate microwave power for accelerating electron beams generated by the respective electron guns in sequence.

According to embodiments of the present technique, each electron gun in the circular electron gun array is arranged on the outer side of the wall of a concentric coaxial cavity that is most outside of the plurality of concentric coaxial cavities.

According to embodiments of the present technique, the CT device may further comprise a transmission unit configured to carry the object to be detected to move along the axis of the circular electron gun array.

According to embodiments of the present technique, the plurality of concentric coaxial cavities is coupled via a coupling hole.

According to embodiments of the present technique, the circular detector array is arranged inside of the circular target and separates from the circular target in the axial direction.

According to embodiments of the present technique, the CT device may further comprise a driving mechanism configured to drive the circular electron gun array to move to and fro a certain degree when each electron gun emits electron beams along the radial direction under the control of the control signal, the degree being less than or equal to the angle between two line, one line connecting one of the electron guns to a center of a circle on which the circular electron gun array is positioned, the other line connecting an adjacent electron gun to the center.

According to embodiments of the present technique, the CT device may further comprise a collimator configured to collimate the X-rays.

According to embodiments of the present technique, each detection unit in the circular detector array is a multi-detector row unit.

According to embodiments of the present technique, there is provided a method for a CT device, comprising steps of emitting, from respective electron guns of a circular electron gun array, electron beams along a radial direction of the circular electron gun array in sequence according to a predetermine pulse sequence; accelerating the electron beams emitted from the respective electron guns of the circular electron gun array in sequence by an acceleration cavity, which acceleration cavity including a plurality of nested concentric coaxial cavities that operate in $\pi$ mode; generating X-rays by the accelerated electron beams bombarding a transmission target; and receiving the X-rays after they have passed through an object to be detected.

According to embodiments of the present technique, the scanning speed of the circular electron gun array is changed by changing the trigger mode of the electron guns.

According to embodiments of the present technique, energy of the X-rays is changed by adjusting the feed power of the microwave power source so as to generate X-ray beams of different energies.

According to embodiments of the present technique, the method may further comprise a step of generating a control signal to control the electron guns in the circular electron gun array to start in sequence, and to control the microwave power source to generate microwave power for accelerating electron beams generated by the respective electron gun in sequence.

According to embodiments of the present technique, the method may further comprise a step of generating a control signal to control a first group of electron guns that are equally spaced in the circular electron gun array to start at a first timing simultaneously, to control a second group of electron guns that are equally spaced in the circular electron gun array to start at a second timing simultaneously, and to control the microwave power source to generate microwave power for accelerating electron beams generated by the respective electron guns in sequence.

According to embodiments of the present technique, the method may further comprise a step of driving the circular electron gun array to move to and fro a certain degree when each electron gun emits electron beams along the radial direction under the control of the control signal, the degree being less than or equal to the angle between two line, one line connecting one of the electron guns to a center of a circle on which the circular electron gun array is positioned, the other line connecting an adjacent electron gun to the center.

According to the solutions above, it can improve the CT scanning speed drastically while ensuring a certain temporal resolution.

BRIEF DESCRIPTION OF THE DRAWINGS

The implementations of the present technique are illustrated in the drawings. The drawings and implementations provide some embodiments of the present technique non-exclusively without limitation, where.

DETAILED DESCRIPTION OF THE EMBODIMENTS

Figure 1:
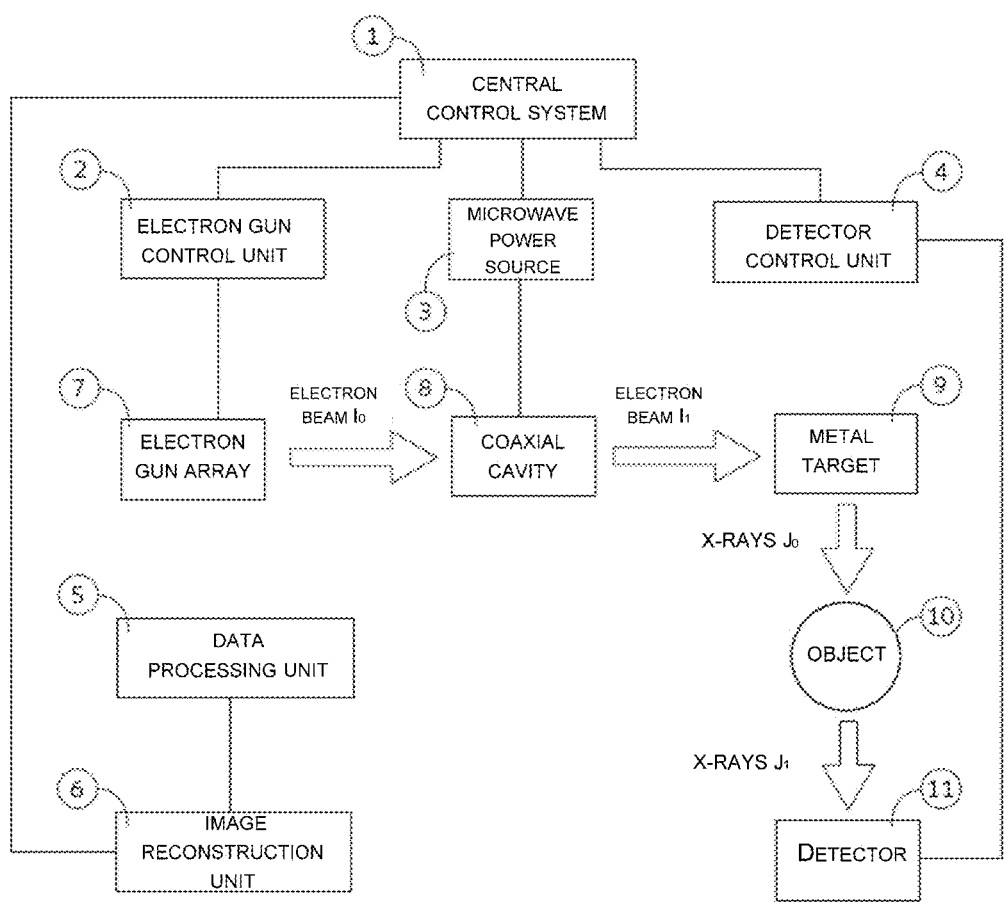
FIG. 1 illustrates a general view of a CT device according to an embodiment of the present technique.

The particular embodiments of the present technique are described below in details. It shall be noted that the embodiments herein are used for illustration only, but not limiting the present technique. In the description below, a number of particular details are explained to provide a better understanding to the present technique. However, it is apparent to those skilled in the art the present technique can be implemented without these particular details. In other examples, well known circuits, materials or methods are not described so as not to obscure the present technique.

Throughout the specification, the reference to "one embodiment," "an embodiment," "one example" or "an example" means that the specific features, structures or properties described in conjunction with the embodiment or example are included in at least one embodiment of the present technique. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that the term "and/or" used herein means any and all combinations of one or more listed items.

In order to further improve the scanning speed of a CT device, according to an embodiment, there is provided a CT device comprising a circular electron gun array including a plurality of electron guns, each of the electron guns is configured to emit electron beams along the radial direction of the circular electron gun array in sequence according to a predetermine pulse sequence; an acceleration cavity disposed inside of a circle on which the circular electron gun array is positioned, including a plurality of nested concentric coaxial cavities that operate in π mode for accelerating electron beams emitted from the respective electron guns of the circular electron gun array; a circular transmission target disposed inside of the circle on which the circular electron gun array is positioned and being bombarded by the accelerated electron beams to generate X-rays; and a circular detector configured to receive the X-rays after they have passed through an object to be detected.

For example, in the CT device according to the embodiment, a circular electron gun array is used as the electron beam source. A coaxial resonance acceleration cavity with a TEM mode is used as the acceleration cavity. The coaxial resonance acceleration cavity is comprised of a plurality of concentric coaxial cavities which operate in π mode. A circular metal transmission target is used as the target. The electron beam source (i.e., the electron gun array) may be arranged at outer side of the coaxial cavity and the metal target may be arranged at inner side of the coaxial cavity. The electron beams are output along the radial direction and bombard the target to generate X-rays.

According to some embodiments, in the Ct device, the electron gun control unit generates a voltage pulse sequence to control the circular electron gun array to generate radial electron beams. Electron beams are accelerated by a coaxial resonance acceleration cavity powered by a microwave power source to have expected energy, which are output in the radial direction and bombard the circular metal transmission target to generate radial X-rays. The X-rays pass through an objected to detected, and are then received by the circular detector, which transmit strength data to a central control system for processing. Furthermore, the electron gun control unit is controlled to change the trigger mode, so as to change the scanning speed. Moreover, the energy of the X-rays can be changed by adjusting feed power of the microwave power source. Accordingly, the present technique is applicable to medical imaging field that requires low-energy X-rays and industry non-destructive detection field that requires high-energy X-rays.

According to another embodiment, in order to cancel the limit on the scanning speed (i.e., the temporal resolution) of the prior CT techniques, there is provided a CT device of a high temporal resolution. It uses a pulse microwave power source of a high repetition frequency (about 1000 pps), so that data collection at a fixed position may be performed more than one thousand times within one macro-pulse of the power source (about 1 μs). The interval between adjacent micro-pulses is about 1 ms, and thus the scanning speed can be up to 1 ms/round, which is 50 times of the scanning speed of the most advanced CT device.

For example, for a coaxial cavity powered by a radio frequency microwave power source of a high repetition frequency, a plurality of direct-current high-voltage electron guns are usually arranged outside of the coaxial cavity and are distributed uniformly along a circle. The respective electron guns are triggered by a pulse sequence in sequence to emit continuous electron beams. The electron beams are accelerated in the TEM field in the coaxial cavity, and then bombard the transmission target to generate a sequence of X-rays that are perpendicular to the axis of the coaxial cavity and pass through the same center. The sequence of X-rays is used to perform CT imaging on an object to be detected.

According to the embodiment that uses the foregoing structure, it may achieve CT imaging of a scanning speed that may be up to 1 ms/round while ensuring a certain spatial resolution. Meanwhile, by adjusting the feed power of the microware power source, the energy of the X-rays may be adjusted in a range, giving a possibility of generating high-energy X-rays which are applicable to the industry non-destructive detection field. For example, X-ray beams of different energies may be generated by accelerating electron beams with different feed powers, and thus multi-energy scanning, for example, dual-energy scanning, can be implemented.

For example, it may output electron beams of different energies, i.e., X-rays of different energies, by adjusting the feed power of the microwave power source. In a certain range, the relation between electron beams and feed power satisfies:

$$E \propto \sqrt{P} \qquad (1)$$

where E is the energy of the electron beam, and P is the feed power. Thus, it may output X-rays of multiple energies.

FIG. 1 illustrates a general view of a CT device according to an embodiment of the present technique. As shown in FIG. 1, the CT device according to the embodiment comprises an electrical scanning unit, a central control system 1, an electron gun control unit 2, a microwave power source 3, a detector control unit 4, a data processing unit 5 and an image reconstruction unit 6. The electrical scanning unit comprises a circular electron gun array 7, a coaxial resonance acceleration cavity 8, a metal target 9 and a circular detector 11.

Figure 2:
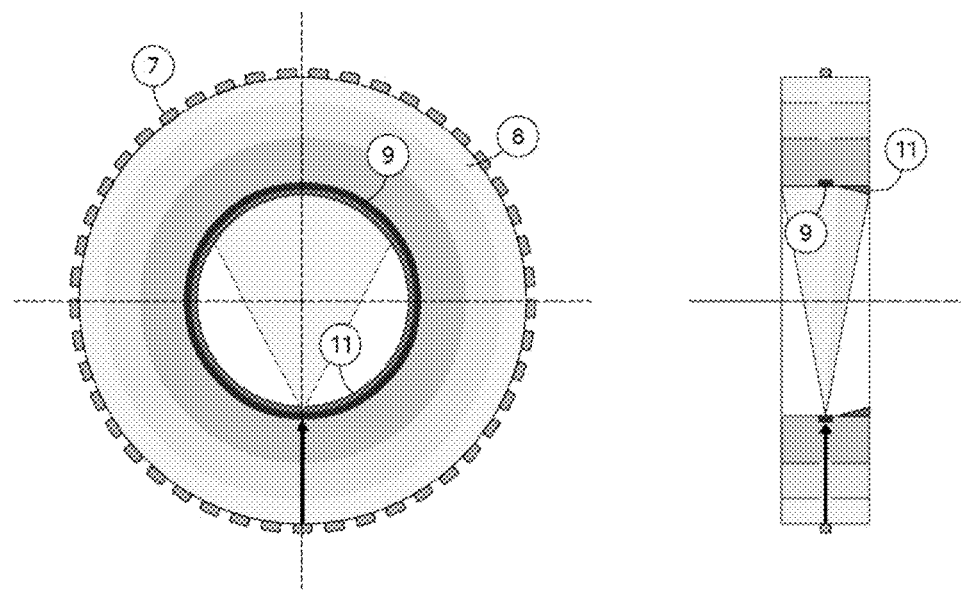
FIG. 2 illustrates a synthesis schematic diagram of an electrical scanning part of a CT device according to an embodiment of the present technique.

The electrical scanning unit is the hardware for implementing ultra-fast CT imaging. As shown in FIG. 2 which illustrates the structure of the electrical scanning unit, the circular electron gun array 7 is composed of a plurality of (typically tens of, or even hundreds of) electron guns that will emit electrons if triggered.

The acceleration cavity 8 operates in TEM mode, and accelerates electrons in the radial direction to have the electrons bombard the metal target 9 to generate X-rays. The circular detector 11 receives X-rays that have passed through an object to be detected 10.

FIG. 2 illustrates the principle of a multi-layer coaxial cavity in a CT device according to an embodiment of the present technique. The left of FIG. 2 depicts the central cross section of the coaxial cavity, and the right of FIG. 2 depicts the central vertical section, the black solid arrow denotes the electron beams, and the gray region at the center denotes X-rays. The circular electron gun array 7 is arranged at outer side of the multi-layer coaxial cavity, and the circular metal transmission target 9 is arranged at inner side of the coaxial cavity 8. The circular detector 11 is also arranged at inner side of the coaxial cavity.

The three colors shown in the coaxial cavity denote three (or more) concentric coaxial cavities that are coupled via a coupling hole. In other embodiments, the plurality of coaxial cavities may be coupled by other ways, for example, via a coupler.

When one electron gun emits electron beams, the electron beams enter the coaxial cavity along the radial direction and are accelerated as they go through the microwave field of the three coaxial cavities in sequence. The electron beams then bombard the transmission target to generate X-rays that are in the same direction as the direction of movement of the electron beams. The X-rays pass through an object to be detected 10, and then project on the detector 11 and are received by detector 11. According to some embodiments, the X-rays that are received by the detector are not X-rays that are exactly along the radial direction, but X-rays that are in a direction that has an angle with respect to the radial direction, i.e., those X-rays shown in dark at the right of the drawing.

Figure 3:
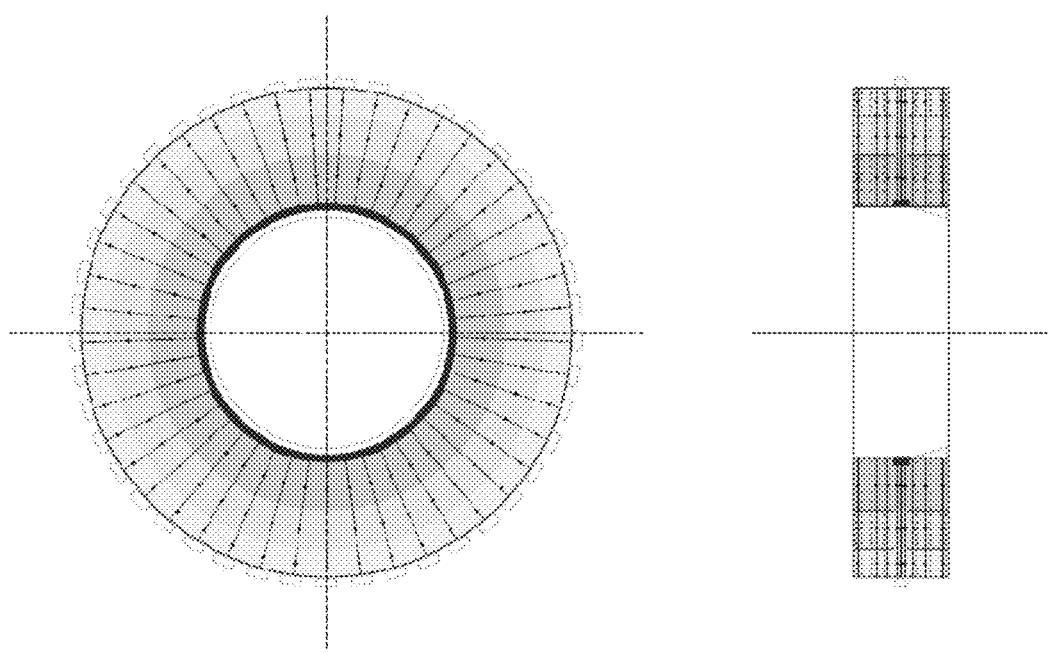
FIG. 3 illustrates a field pattern when a coaxial cavity operates in a CT device according to an embodiment of the present technique.

FIG. 3 illustrates a field pattern of a multi-layer coaxial cavity in a CT device according to an embodiment of the present technique. The left of FIG. 3 depicts the central cross section of the coaxial cavity, and the right of FIG. 3 depicts the central vertical section, the black solid arrow denotes the electrical field, x and • in black denote the magnetic field.

The field pattern in each coaxial cavity is TEM mode, and the coupled cavities operate in π mode. Thus, two adjacent coaxial cavities have electromagnetic fields that are out of phase. The TEM mode in the coaxial cavity has the following characteristics: the electrical field has only longitudinal components, and the magnetic field has only axial components; the electromagnetic field is uniform along the axial direction; the electrical field is maximal at the central cross section of the electron beams, and the magnetic field is 1 at the position. The relativistic velocity 13 of the electrons gradually increases and approaches 1 during the acceleration. In order to always synchronize the microwave field of the coaxial cavities that operate in π mode with the electrons (that is, the electrons are always in the acceleration phase), the radial size of the concentric coaxial cavities much gradually increase from outside to inside, until to the half wavelength of the operating microwaves in the cavities. This is also shown in the drawing.

According to embodiments of the present technique, the central control system 1 in the CT device connects to the electron gun control unit 2 and the microwave power source 3, and generates a control signal to control the electron guns in the circular electron gun array 7 to start in sequence, and to control the microwave power source 3 to generate microwave power for accelerating electron beams generated by the respective electron guns in sequence.

According to other embodiments of the present technique, the central control system 1 in the CT device connects to the electron gun control unit 2 and the microwave power source 3, and generates a control signal to control electron guns that are equally spaced in the circular electron gun array 7 to start simultaneously, and to control the microwave power source 3 to generate microwave power for accelerating electron beams generated by the respective electron guns in sequence.

In performing imaging, as shown in FIG. 1, the electron gun control unit 2 receives a scanning start command from the central control system 1, and controls the electron guns of the circular electron gun array 7 to emit electron beams $I_0$ in sequence (according to the electron acceleration energy and design of the collimator, 1~3 electron guns are allowed to emit electrons at the same time to expedite the scanning speed). The electron beams $I_0$ are accelerated in the coaxial resonance acceleration cavity 8 to have expected energy (dependent on the feed power of the microware power source 3, and may be low to 100 keV, or be up to 1 MeV). The accelerated electron beams $I_1$ bombard the metal transmission target 9 to generate X-rays $J_0$ that are perpendicular to the axis of the coaxial cavity, collimated by a collimator (not shown) between the metal transmission target 9 and the detector 11, and pass through an object to be detected 10 that is carried on a transmission unit. The attenuated X-rays are received by the circular detector 11. The transmission unit moves along the axis of the circular electron gun array.

The detector control unit 4 receives a scanning start instruction from the central control unit 1, and controls the circular detector 11 to collect data and transmit the data to the central control unit 1. The central control unit re-arranges the collected detector data according to the emission sequence of the electron guns, and transmit the data to the data processing unit 5 for pre-processing. The data processing unit 5 performs processing such as non-uniformity correction, hardening correction, brightness correction, and so on, and transmits the processed standard projection data to the image reconstruction unit 6 for reconstruction, and thereby a sequence of CT images of specific positions of the object to be detected can be obtained.

In some embodiments, the metal target 9 and the detector 11 cannot be disposed at the same longitudinal position in the real installation, and thus the X-rays generated by bombardment of the electron beams arrive at the surface of the detector obliquely. Accordingly, it needs to incline the surface of the detector to have it perpendicular to the incident direction of the X-rays that project on its surface. Moreover, the circular detector is arranged to separate from the metal target by a distance, so as to receive X-rays that project obliquely from the opposite metal target, as shown in FIG. 2

In some embodiments, the electron guns are equally spaced in a circle. In order to facilitate the subsequent scanning, different data are obtained when the electron guns emit electron beams sequentially. For example, the number of electron guns is configured to be odd, so that there would not be two opposite electron guns, i.e., there are no such two electron guns that the angle between two lines, one connecting one electron gun to the center of the circle, the other connecting the other electro gun to the center of the circle, is 180°. Thus, the obtained data would not repeat with each other. In other words, the density of the electron guns becomes high, and thus the spatial resolution is enhanced.

In some embodiments, the CT device operates in more than one operation mode. It depends on the structure of the electron source, which is also an advantage of the CT device according to the present technique over the other CT devices. For example, the electron guns may operate in a single electron gun operation mode, i.e., the common mode where the control unit generates a pulse sequence to trigger respective electron guns in sequence, and only one electron gun is emitting electrons at any time. The electron beams bombard the metal target, and X rays are emitted from the target point, which pass through the object and are then received by the detector, to obtain the data. If it is to scan the whole slice, all the electron guns are triggered in sequence, i.e., the target point rotates 360°.

In some embodiments, the CT device may operate in a multiple electron gun operation mode. At the same time, a plurality of equally spaced electron guns is triggered to image the object, so that the detector can obtain data. For example, in a three electron gun operation mode, each target point needs to rotate only 120° to scan the whole slice. Again, for example, in a six electron gun operation mode, each target point needs to rotate only 60° to scan the whole slice.

For example, in some embodiments, the control system (for example the central control system as shown) connects to the circular electron gun array and the microwave power source, and generates a control signal to control the electron beam emission units in the circular electron beam emission array to start in sequence, and to control the microwave power source to generate microwave power for accelerating electron beams generated by the respective electron beam emission units in sequence.

In other embodiments, the control system connects to the circular electron beam emission array and the microwave power source and generates a control signal to control a first group of electron beams emission units (the electron guns No. 1, 4, 7, . . . ) that are equally spaced in the circular electron beam emission array to start at a first timing simultaneously, to control a second group of electron beam emission units (the electron guns No. 2, 5, 8, . . . ) that are equally spaced in the circular electron beam emission array to start at a second timing simultaneously, to control a third group of electron beam emission units (the electron guns No. 3, 6, 9, . . . ) that are equally spaced in the circular electron beam emission array to start at a third timing simultaneously, and to control the first group of electron beam emission units (the electron guns No. 1, 4, 7, . . . ) that are equal spaced in the circular electron beam emission array to start at a fourth timing simultaneously, so that the emitted electron beams are "rotated." Meanwhile, the control unit also controls the microwave power source to generate microwave power for accelerating electron beams generated by the respective electron beam emission units in sequence.

Although the multiple electron gun operation mode may bring several advantages, for example enhancement of temporal resolution, reduction of the time required for scanning a single slice, the number of electron guns that operate at the same time cannot be too much because X-rays emitted from a single target point has a scattering angle and thus one point at the detector may receive data from more than one target point, and thereby an interference and distortion may arise.

In some embodiments, a driving mechanism is provided to drive the electron guns to wriggle, i.e., the wriggle mode of the electron guns. The term "wriggle" means that the circle where the electron guns array is located move to and fro a certain small degree. The mode has an advantage of improving spatial resolution. For example, rotating the electron gun array for a small angle counter clock wise has the following result: the target point rotates along with the circle of the electron guns, and thus the emitted X-rays now may cover a range where the previous X-rays cannot cover otherwise. From that point of view, the "wriggle" of the electron guns makes the density of the electron guns array double. The more the times of the electron emission during "wriggle" is, the more the density is, and the higher the spatial resolution of the CT device is.

For example, in some embodiments, a driving mechanism provided to drive the circular electron beam transmission array to move to and fro a certain degree when each electron gun emits electron beams along the radial direction in sequence under the control of a control signal, the degree being less than or equal to the angle between two lines, one line connecting one of the electron guns to a center of a circle on which the circular electron gun array is positioned, the other line connecting an adjacent electron gun to the center.

In some embodiments, there is provided a method for a CT device, comprising steps of emitting, from respective electron guns of a circular electron gun array, electron beams along a radial direction of the circular electron gun array in sequence according to a predetermine pulse sequence; accelerating the electron beams emitted from the respective electron guns of the circular electron gun array in sequence by an acceleration cavity, which acceleration cavity including a plurality of nested concentric coaxial cavities that operate in π mode; generating X-rays by the accelerated electron beams bombarding a transmission target; and receiving the X-rays after they have passed through an object to be detected.

According to some embodiments of the present technique, the scanning speed of the circular electron gun array is changed by changing the trigger mode of the electron guns.

According to some embodiments of the present technique, energy of the X-rays is changed by adjusting the feed power of the microwave power source so as to generate X-ray beams of different energies.

According to some embodiments of the present technique, the method may further comprise a step of generating a control signal to control the electron guns in the circular electron gun array to start in sequence, and to control the microwave power source to generate microwave power for accelerating electron beams generated by the respective electron gun in sequence.

According to some embodiments of the present technique, the method may further comprise a step of generating a control signal to control a first group of electron guns that are equally spaced in the circular electron gun array to start at a first timing simultaneously, to control a second group of electron guns that are equally spaced in the circular electron gun array to start at a second timing simultaneously, and to control the microwave power source to generate microwave power for accelerating electron beams generated by the respective electron guns in sequence.

According to some embodiments of the present technique, the method may further comprise a step of driving the circular electron gun array to move to and fro a certain degree when each electron gun emits electron beams along the radial direction under the control of the control signal, the degree being less than or equal to the angle between two line, one line connecting one of the electron guns to a center of a circle on which the circular electron gun array is positioned, the other line connecting an adjacent electron gun to the center.

The present technique utilizes a pulse signal to trigger respective electron guns in a circular electron gun array to emit electron beams, and thus the scanning speed may be adjusted by changing the triggering delay and the triggering mode (for example, a single-gun trigger or a multi-gun trigger). The limit on the scanning speed in the present technique mainly depends on the dead time of the detector, the repetition frequency of the pulse power source and the flow strength of the electron gun. Considering the existing technology, the present technique can achieve a scanning period less than 1 ms.

What shall be noted is that although the present technique is mainly applicable to the medical imaging, it is possible to apply it to the medical treatment or non-destructive detection field that require high energy X-rays due to the adjustment of the energy of X-rays.

Although an electron gun array is used to generate electron beams along the radial direction in the embodiment, other electron beam generation units are also possible.

The foregoing detailed description has set forth various embodiments of the CT device and method of the same via the use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present technique has been described with reference to several typical embodiments, it is apparent to those skilled in the art that the terms are used for illustration and explanation purpose and not for limitation. The present technique may be practiced in various forms without departing from the esprit or essence of the present technique. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present technique which is defined by the claims as attached.

What is claimed is:

1. A CT device comprising
a circular electron gun array including a plurality of electron guns, each of the electron guns is configured to emit electron beams along the radial direction of the circular electron gun array in sequence according to a predetermine pulse sequence;
an acceleration cavity disposed inside of a circle on which the circular electron gun array is positioned, including a plurality of nested concentric coaxial cavities that operate in $\pi$ mode for accelerating electron beams emitted from the respective electron guns of the circular electron gun array;
a circular transmission target disposed inside of a circle on which the acceleration cavity is positioned and being bombarded by the accelerated electron beams to generate X-rays; and
a circular detector configured to receive the X-rays after they have passed through an object to be detected.

2. The CT device according to claim 1, further comprising:
an electron gun control unit connected to the circular electron gun array and configured to generate the pulse sequence to control the circular electron gun array to generate electron beams that are emitted along the radial direction;
a microwave power source connected to the acceleration cavity so that the electron beams are accelerated along the radial direction to have expected energy and bombard the circular transmission target to generate radial X-rays.

3. The CT device according to claim 2, wherein the electron gun control unit is controlled to change a trigger mode so as to change the scanning speed of the circular electron gun array.

4. The CT device according to claim 2, wherein the feed power of the microwave power source is adjusted to change the energy of the X-rays so as to generate X-ray beams of different energies.

5. The CT device according to claim 2, further comprising a control system coupled to the electron gun control unit and the microwave power source, and configured to generate a control signal to control the electron guns in the circular electron gun array to start in sequence and to control the microwave power source to generate microwave power for accelerating electron beams generated by the respective electron gun in sequence.

6. The CT device according to claim 2, further comprising a control system connected to the electron gun control unit and the microwave power source, and configured to generate the control signal to control a first group of electron guns that are equally spaced in the circular electron gun array to start at a first timing simultaneously, to control a second group of electron guns that are equally spaced in the circular electron gun array to start at a second timing simultaneously, and to control the microwave power source to generate microwave power for accelerating electron beams generated by the respective electron guns in sequence.

7. The CT device according to claim 2, wherein each electron gun in the circular electron gun array is arranged on the outer side of the wall of a concentric coaxial cavity that is most outside of the plurality of concentric coaxial cavities.

8. The CT device according to claim 1, further comprising a transmission unit configured to carry the object to be detected to move along the axis of the circular electron gun array.

9. The CT device according to claim 1, wherein the plurality of concentric coaxial cavities is coupled via a coupling hole.

10. The CT device according to claim 1, wherein the circular detector array is arranged inside of the circular target and separates from the circular target in the axial direction.

11. The CT device according to claim 1, further comprising a driving mechanism configured to drive the circular electron gun array to move to and fro a certain degree when each electron gun emits electron beams along the radial direction under the control of the control signal, the degree being less than or equal to the angle between two line, one line connecting one of the electron guns to a center of a circle on which the circular electron gun array is positioned, the other line connecting an adjacent electron gun to the center.

12. The CT device according to claim 1, further comprising a collimator configured to collimate the X-rays.

13. The CT device according to claim 1, wherein each detection unit in the circular detector array is a multi-detector row unit.

14. A method for a CT device, comprising steps of
emitting, from respective electron guns of a circular electron gun array, electron beams along a radial direction of the circular electron gun array in sequence according to a predetermine pulse sequence;
accelerating the electron beams emitted from the respective electron guns of the circular electron gun array in sequence by an acceleration cavity, which acceleration cavity including a plurality of nested concentric coaxial cavities that operate in π mode;
generating X-rays by the accelerated electron beams bombarding a transmission target; and
receiving the X-rays after they have passed through an object to be detected.

15. The method according to claim 14, wherein the scanning speed of the circular electron gun array is changed by changing the trigger mode of the electron guns.

16. The method according to claim 14, wherein energy of the X-rays is changed by adjusting the feed power of the microwave power source so as to generate X-ray beams of different energies.

17. The method according to claim 14, further comprising a step of generating a control signal to control the electron guns in the circular electron gun array to start in sequence, and to control the microwave power source to generate microwave power for accelerating electron beams generated by the respective electron gun in sequence.

18. The method according to claim 14, further comprising a step of generating a control signal to control a first group of electron guns that are equally spaced in the circular electron gun array to start at a first timing simultaneously, to control a second group of electron guns that are equally spaced in the circular electron gun array to start at a second timing simultaneously, and to control the microwave power source to generate microwave power for accelerating electron beams generated by the respective electron guns in sequence.

19. The method according to claim 14, further comprising a step of driving the circular electron gun array to move to and fro a certain degree when each electron gun emits electron beams along the radial direction under the control of the control signal, the degree being less than or equal to the angle between two line, one line connecting one of the electron guns to a center of a circle on which the circular electron gun array is positioned, the other line connecting an adjacent electron gun to the center.

* * * * *